US008868164B2

(12) United States Patent
Kabakov et al.

(10) Patent No.: US 8,868,164 B2
(45) Date of Patent: Oct. 21, 2014

(54) FETAL MONITORING DEVICE AND METHOD

(71) Applicant: General Electric Company, Schenectady, NY (US)

(72) Inventors: Serguei Kabakov, Savage, MD (US); Steven M. Falk, Baltimore, MD (US); Bradley C. Fox, West Valley City, UT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/783,783

(22) Filed: Mar. 4, 2013

(65) Prior Publication Data

US 2014/0249436 A1    Sep. 4, 2014

(51) Int. Cl.
| | |
|---|---|
| A61B 5/04 | (2006.01) |
| A61B 5/0408 | (2006.01) |
| A61B 5/00 | (2006.01) |
| A61B 5/11 | (2006.01) |
| A61B 5/0402 | (2006.01) |

(52) U.S. Cl.
CPC .............. *A61B 6/6806* (2013.01); *A61B 5/742* (2013.01); *A61B 5/11* (2013.01); *A61B 5/721* (2013.01); *A61B 5/0402* (2013.01); *A61B 5/746* (2013.01); *A61B 5/4325* (2013.01)
USPC ........................................................ 600/511

(58) Field of Classification Search
None
See application file for complete search history.

(56) References Cited

U.S. PATENT DOCUMENTS

| | | | |
|---|---|---|---|
| 4,781,200 A | 11/1988 | Baker | |
| 5,069,218 A | 12/1991 | Ikeda | |
| 5,442,940 A | 8/1995 | Secker et al. | |
| 5,458,122 A * | 10/1995 | Hethuin | 600/509 |
| 5,609,156 A | 3/1997 | Keith et al. | |
| 5,954,663 A | 9/1999 | Gat | |
| 5,957,855 A | 9/1999 | Oriol et al. | |
| 6,254,537 B1 | 7/2001 | Nguyen | |
| 6,540,673 B2 * | 4/2003 | Gopinathan et al. | 600/300 |
| 6,751,498 B1 * | 6/2004 | Greenberg et al. | 600/511 |
| 7,113,819 B2 | 9/2006 | Hamilton et al. | |
| 7,818,050 B2 * | 10/2010 | Rapoport et al. | 600/511 |
| 7,828,753 B2 | 11/2010 | Eucliano, II et al. | |
| 7,949,389 B2 * | 5/2011 | Wolfberg et al. | 600/511 |
| 2007/0191728 A1 * | 8/2007 | Shennib | 600/546 |
| 2008/0058656 A1 * | 3/2008 | Costello et al. | 600/508 |
| 2009/0192396 A1 | 7/2009 | Hayes-Gill et al. | |
| 2010/0274145 A1 * | 10/2010 | Tupin et al. | 600/511 |

OTHER PUBLICATIONS

Piezo Film Sensors Technical Manual; Measurement Specialities™; Measurement Specialties, Inc., Hampton, VA , Mar. 2008.

(Continued)

*Primary Examiner* — Brian T Gedeon
(74) *Attorney, Agent, or Firm* — Andrus Intellectual Property Law, LLP

(57) ABSTRACT

A fetal monitoring device includes a piezofilm sheet, a first electrode, and a second electrode. A controller is operably connected to the piezofilm sheet, first electrode, and second electrode and receives a biopotential and a piezofilm signal. The controller derives at least one of a maternal heart rate and a uterine activity for the biopotential and derives at least one of a fetal heart rate and fetal motion detection from the piezofilm signal. The controller derives an index of fetal health and operate an indicator to present the derived index of fetal health.

20 Claims, 8 Drawing Sheets

(56) References Cited

OTHER PUBLICATIONS

Piezo Film Product Guide and Price List; Measurement Specialties (MEAS), Hampton, VA Aug. 1, 2008.

Kovacs, F. et al; Extended Noninvasive Fetal Monitoring by Detailed Analysis of Data Measured with Phonocardiography Abstract; Biomedical Engineering IEEE Transactions; Jan. 2011.

Bakker, P.C.A.M. et al; The quality of intrapartum fetal heart rate monitoring Abstract; Department of Obstetrics and Gynecology; Vrije University Medical Center; The Netherlands; Accepted Jan. 6, 2004.

Choosing Sensors for Medical Applications; Measurement Specialties™; Fremont, CA; Jan. 2013.

Matthews, Robert et al; The invisible electrode—zero prep time, ultra low capacitive sensing; Quantum Applied Science and Research; San Diego, CA; undated.

Park, Chulsung et al; An Ultra-Wearable, Wireless, Low Power ECG Monitoring System; University of California and Quantum Applied Science & Research, Inc.; undated.

Sameni, Reza et al; A Review of Fetal ECG Signal Processing; Issues and Promising Directions; pp. 1-30.

Chen, H.Y. et al; Electronic fetal heart rate monitoring and its relationship to neonatal and infant mortality in the United States Abstract; Am. J. Obstet. Gynecol.; Apr. 20, 2011; Center for Urban Population Health, Milwaukee, WI, USA.

Devane, A.Z. et al; Continuous cardiotocography (CTG) as a form of electronic fetal monitoring (EFM) for fetal assessment during labour (Review); Copyright 2007; The Cochrane Colaboration; Published by John Wiley & Sons, Ltd.; pp. 1-81.

Warrick, P.A. et al; Classification of normal and hypoxic fetuses from systems modeling of intrapartum cardiotocography Abstract; IEEE Trans. Biomed Engineering; vol. 4; Published Apr. 2010.

Sweha, A., M.D. et al; Interpretation of the Electronic Fetal Heart Rate During Labor.

\* cited by examiner

FETAL MONITORING DEVICE AND METHOD

BACKGROUND

The present disclosure is related to the field of fetal monitoring. More specifically, the present disclosure is related to a device and method for fetal monitoring.

Fetal monitors often combine multiple technologies in order to acquire physiological parameters of the fetus in which a highly trained clinician such as a nurse or doctor would find interesting in evaluating the health of the fetus. These technologies and parameters include Doppler ultrasound to detect fetal heart rate and fetal motion detection, tocodynamometry to detect uterine activity, pulse oximetry to detect maternal heart rate and vibro-acoustic stimulation to "wake up" the fetus.

While each of these parameters are considered useful to the trained clinician, the combination of these technologies currently used to acquire these parameters present significant challenges. Doppler ultrasound is limited in ability to detect short term variability in fetal heart rate, which can be an indicator of fetal stress. Doppler ultrasound is further susceptible to frequent signal loss due to maternal/fetal movements which causes gaps in the FHR tracings. Toco and Doppler are also inconvenient as they are limited in ability to monitor obese patients. Furthermore, the use of these complex technologies require highly trained clinicians in order to properly position and prepare the patient's skin for each of these devices to obtain meaningful physiological measurements, as well as to interpret the readings from these physiological measurements.

BRIEF DISCLOSURE

An exemplary embodiment of a fetal monitoring device includes a piezofilm sheet, a first electrode, and a second electrode. A controller is operably connected to the piezofilm sheet, the first electrode, and the second electrode. The controller receives an acoustic signal from the piezofilm sheet and a biopotential measured between the first electrode and the second electrode. The controller derives at least one of fetal heart rate and fetal motion detection from the acoustic signal and at least one maternal heart rate and uterine activity from the biopotential. The controller calculates an index of fetal health from the at least one of fetal heart rate and fetal motion detection and at least one of maternal heart rate and uterine activity. A visual indicator is operable by the controller to present the calculated index of fetal health.

An exemplary alternative embodiment of a fetal monitoring device includes at least one glove configured to be worn by a patient. The glove includes a forehand side, a backhand side, a thumb region, and at least one finger region. A piezofilm sheet is secured to an exterior of the forehand side of the at least one glove. A first electrode is secured to the forehand side of the thumb region. A second electrode is secured to the forehand side of at least one finger region. A controller is electrically connected to the piezofilm, the first electrode, and the second electrode. The controller receives an acoustic signal from the piezofilm sheet and a biopotential measured between the first electrode and second electrode. The controller derives a fetal heart rate and a fetal motion detection from the piezofilm signal and derives a maternal heart rate and a uterine activity from the biopotential. The controller derives an index of fetal health from the fetal heart rate, the fetal motion detection, the maternal heart rate, and the uterine activity. A visual indicator is operable by the controller to present the index of fetal health.

An exemplary embodiment of a method of monitoring the health of a fetus includes providing a mother with a wearable garment. The wearable garment includes a piezofilm sheet, a first electrode, a second electrode, and a controller. The controller receives a biopotential between the first electrode and the second electrode. The controller receives an acoustic signal from the piezofilm. The controller derives at least one of fetal heart rate and fetal motion detection from the received acoustic signal. The controller derives at least one of maternal heart rate and uterine activity from the biopotential. The controller derives an index of fetal health from the derived at least one of fetal heart rate and fetal motion detection and at least of one of maternal heart rate and uterine activity. The derived index of fetal health is visually presented.

DETAILED DESCRIPTION OF THE INVENTION

Current fetal monitoring solutions require expert interpretation of the fetal and maternal signals acquired by those devices. In a setting such as at home care or in between in clinic obstetrics appointments, a mother may be interested in monitoring the condition of the fetus. In other instances, a medical care facility may employ staff to attend to the needs of a pregnant patient, but such staff may not have the training to interpret the complex fetal heart rate and uterine activity signals. A solution that places initial fetal and maternal monitoring under the control of the mother and provides an easy-to-understand interpretation of maternal and fetal health is desired.

Embodiments disclosed herein of a device and method of a self-care maternal and fetal transducer with a signal processor that evaluates the acquired maternal and fetal signals in order to produce an evaluation of fetal health without the need for expert interpretation of fetal or maternal signal tracings. In an embodiment, the acquired signals are evaluated to determine whether the patterns found therein are reassuring or non-reassuring. Only the identification of non-reassuring patterns result in an indication that the mother or limited skill nurse should seek more expert medical attention.

Exemplary embodiments as disclosed herein combine biopotentials (ECG/EMG) as acquired by dry electrodes (for electrocardiography (ECG) and uterine electromyography (uEMG) along with acoustic signals acquired with a piezofilm for phonocardiography (PCG). Thus, in an embodiment, these two sensors (the pair of dry electrodes and the piezofilm) are used to derive fetal physiological parameters of fetal heart rate (FHR) and fetal motion detection (FMD) and maternal parameters including uterine activity (UA) and maternal heart rate (MHR), all of which are used to determine fetal health. In some cases, it is to be noted that these parameters are waveforms as the parameters are monitored as functions of time. Exemplary embodiments also operate the piezofilm to generate a final acoustic stimulation signal.

As disclosed in further detail herein, a controller in the device applies one or more algorithms to the acquired maternal and fetal physiological parameters in order to determine whether the parameters represent reassuring patterns of fetal health or non-reassuring patterns of fetal health. The controller produces an indication of the determined fetal health by operation of an indicator, such indicator may be a visual indicator such as one or more light emitting diodes (LEDs) or a liquid crystal display (LCD), an audio indicator such as a sound from a speaker, or a tactile indication such as a vibration exemplarily from an oscillatory device.

Figure 1:
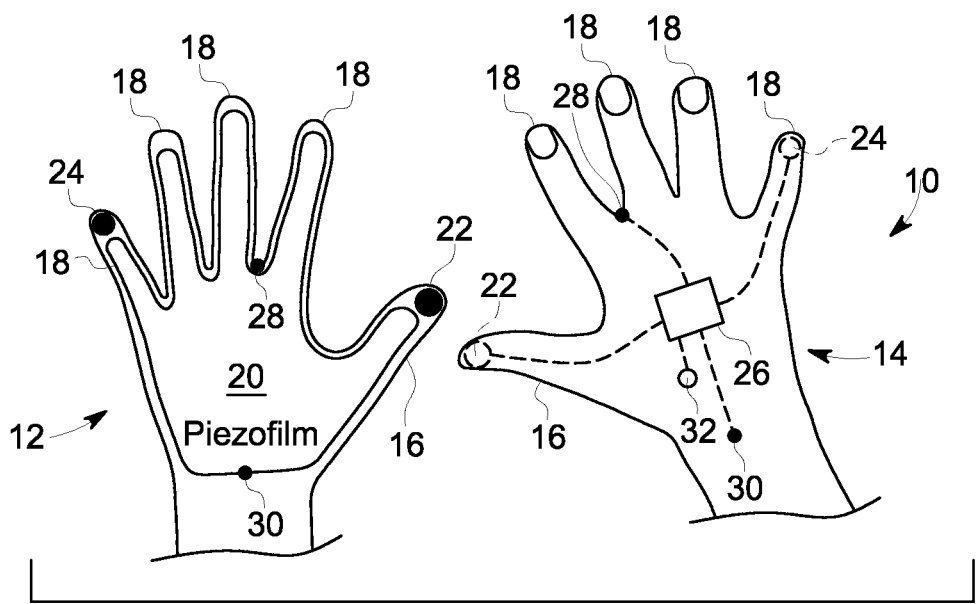
FIG. 1 depicts front and back views of an exemplary embodiment of a fetal monitoring device.

FIG. 1 depicts front and back views of an exemplary embodiment of a fetal monitoring device 10 as disclosed herein. In the embodiment of the fetal monitoring device 10, the fetal monitoring device is incorporated into a glove to be worn by the patient. While the embodiments as disclosed herein all focus on fetal monitoring devices incorporated into a glove or gloves to be worn by a patient, alternative embodiments may be configured to be worn by the patient in another manner, and exemplarily through the use of a belt, or another garment.

The fetal monitoring device 10 includes a front or forehand side 12 and a back or backhand side 14. As previously mentioned above, the embodiment of the fetal monitoring device 10 is formed as a glove, meaning that the fetal monitoring device 10 includes at least one thumb region 16 configured to receive the patient's thumb therein and at least one finger region 18 configured to receive at least one finger of the patient. It will be appreciated that in FIG. 1, the embodiment depicted therein includes a thumb region 16 and four separate finger regions 18; however, if an embodiment only contained a single finger region that receives all of the fingers of the patient, such an embodiment may be commonly recognized as a mitten, although such would be considered to be a glove as used herein. It is to be recognized that this alternative embodiments of gloves as used herein may include fingerless gloves or other such gloves that while receiving the hand, thumb, and fingers of the patient may not cover the entirety of these body parts. While the fetal monitoring device 10 is depicted as a right-handed glove, it is to be recognized that alternative embodiments may be left-handed.

A piezofilm 20 is secured to the forehand side 12 of the fetal monitoring device 10. In a non-limiting embodiment, the piezofilm 20 may be a metallized piezofilm sheet available from Measurement Specialties, Inc., 1000 Lucas Way, Hampton, Va. 23666. In embodiments, the piezofilm 20 may cover the entirety of the forehand side 12, or only a portion thereof, exemplarily, but not limited to the palm of the forehand side. In embodiments, the piezofilm may construct the forehand side of the fetal monitoring device 10, or may be secured to another piece of material that is located between the piezofilm 20 and the hand of the patient.

The fetal monitoring device 10 further includes a first electrode 22 and a second electrode 24. In an embodiment, one of the first electrode 22 or the second electrode 24 is located on the thumb region 16 and the other of the first electrode 22 or the second electrode 24 is located on a finger region 18 of the fetal monitoring device 10. In a non-limiting embodiment depicted in FIG. 1, such electrodes may be located on the tip of the thumb region 16 and the tip of a finger region 18 configured to receive the pinky finger of the patient. In alternative embodiments, the first electrode 22 and second electrode 24 may be located elsewhere on the device, such as, but not limited to at the base of the palm and the tip of the middle finger on the forehand side 12. It is further to be noted that, in the embodiment depicted, the first electrode 22 and the second electrode 24 are located on the forehand side 12 of the fetal monitoring device 20 such as to facilitate use as described in further detail herein.

In an embodiment, the first electrode 22 and second electrode 24 are dry electrodes such that no conductive gel or abrasive skin preparation is required for the electrodes to obtain the biopotential signal as described herein. In embodiments, the biopotential is a combination of ECG and uEMG. As further described, the biopotential signal is adequately obtained with dry electrode technology and dry electrodes eliminate the need for the maternal patient to be concerned with conductive gels or other skin preparation.

In the embodiment depicted in FIG. 1, the backhand side 14 of the fetal monitoring device 10 includes the communicative connections and other circuitry incorporated in the fetal monitoring device 10. It will be understood that this location of the circuitry described herein is merely exemplarily and such circuitry may be located in other configurations as appreciated by one of skill in the art. The backhand side 14 includes a controller 26 that is communicatively connected to the first electrode 22 and second electrode 24 as well as to a first piezofilm contact 28 and a second piezofilm contact 30. In embodiments, the first piezofilm contact 28 and the second piezofilm contact 30 are operable such that the controller 26 receives signals acquired from the piezofilm 20, and also facilitate signals that are transmitted from the controller 26 to the piezofilm 20 as described in more detail herein.

The controller 26 receives the signals from the structures as described above and processes those signals in manners as described in further detail herein. The controller 26 can be implanted in software operated by a processor, analog circuitry, or a combination of both to carry out the functions and operations as described herein. The controller applies one or more algorithms to the acquired signals in order to determine whether the acquired signals represent reassuring or non-reassuring patterns such as to derive an index of fetal health. After determining the index of fetal health, exemplarily whether the patterns represent reassuring or non-reassuring patterns, the controller operates an indicator 32 such as to present the derived index of fetal health. Such an indicator 32 may be implemented as any of a variety of indicators, including, but not limited to, one or more light emitting diodes (LEDs) or LCD display to provide visual indications. In embodiments, the indicator 32 can be part of the controller 26.

Alternatively, or in addition to visual indications, an audible or tactile indication may be provided such as from a speaker to provide an audible output or an eccentric oscillator to provide a vibration or tactile output.

Figure 2:
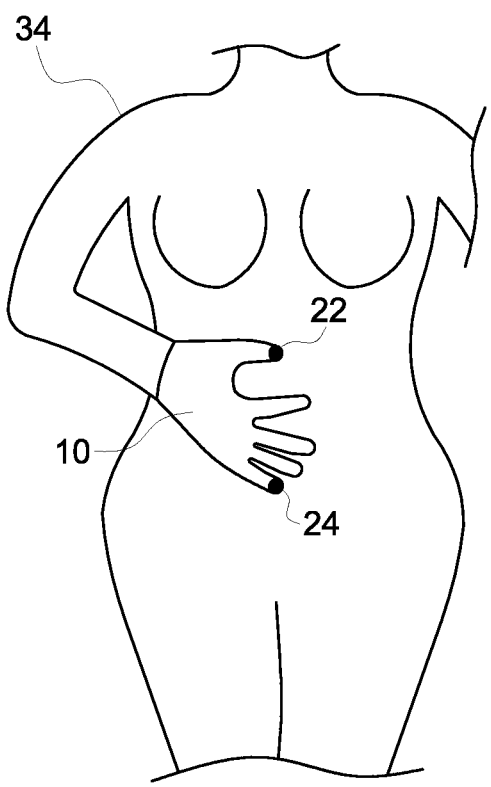
FIG. 2 diagrammatically depicts maternal use of an exemplary embodiment of a fetal monitoring device.

FIG. 2 diagrammatically depicts a maternal patient 34 in use of an exemplary embodiment of the fetal monitoring device 10 of FIG. 1. It is to be noted that one of the embodiments depicted in FIGS. 1 and 2 is configured to wear on the right hand of the maternal patient 34, alternative embodiments configured for use on the left hand of a maternal patient are also contemplated.

FIG. 2 depicts exemplary use and placement of the fetal monitoring device 10 over the abdomen of the maternal patient 34. Such placement exemplarily may position the patient's palm (and the piezofilm 20) over the fetus, while the first electrode 22 and the second electrode 24 are stretched apart at a maximum distance across the fetus and uterus. The operation of the embodiment depicted in FIGS. 1 and 2 will be described herein in further detail with respect to the schematic diagram provided at FIG. 5.

Figure 3:
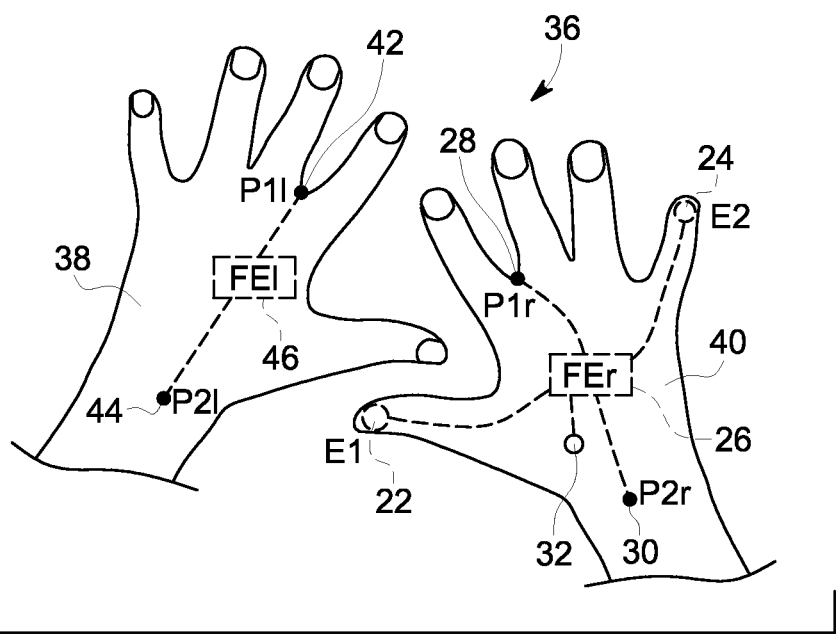
FIG. 3 depicts an alternative exemplary embodiment of a fetal monitoring device.
Figure 4:
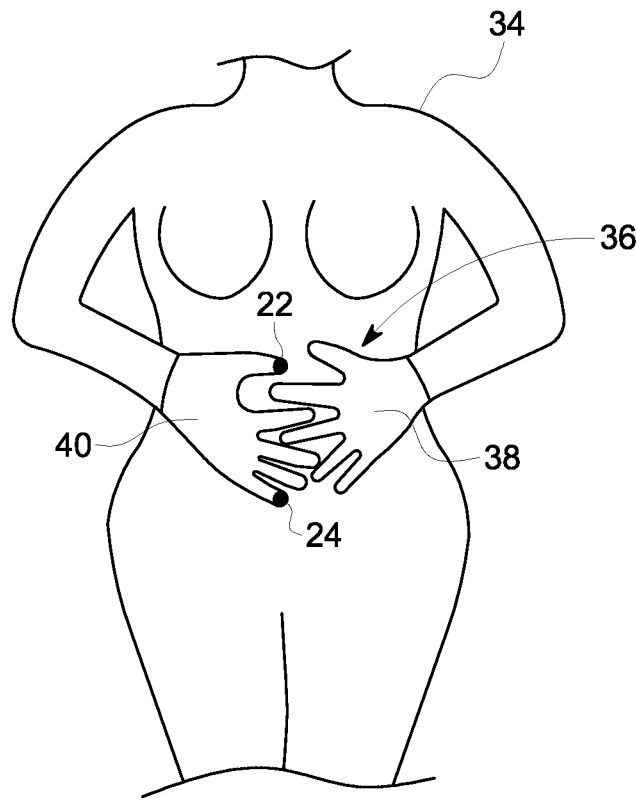
FIG. 4 diagrammatically depicts maternal use of the alternative exemplary embodiment of a fetal monitoring device.

FIGS. 3 and 4 depict an alternative two-handed embodiment of a fetal monitoring device 36. As shown in FIG. 3, which depicts the backhand side of a left glove 38 and a right glove 40 to be worn on the hands of a maternal patient 34. As can be seen from the embodiment of the fetal monitoring device 36 depicted in FIG. 3 compared to the fetal monitoring device 10 depicted in FIG. 1, the right hand gloves in both embodiments are similarly configured with first electrode 22, a second electrode 24, a controller 26, a first piezofilm contact 28, a second piezofilm contact 30, and an indicator 32. The left hand glove 38 includes an additional piezofilm with a third piezofilm contact 42 and a fourth piezofilm contact 44, both of which are connected to a second controller 46. Although it will be recognized in alternative embodiments, the second controller 46 may alternatively be a more simplified circuitry such as described herein, and wherein in an exemplary embodiment, the circuitry in place of second controller 46 is merely directed towards the transmission (e.g. wireless transmission) of the acquired signals to the controller 26. It will be recognized that in alternative embodiments, the circuitry features depicted in the fetal monitoring device 36 of FIG. 3 may be reversed, such that the left hand glove 38 incorporates more components than the right hand glove.

FIG. 4 diagrammatically depicts a maternal patient using the alternative embodiment of the fetal monitoring device 36 showing exemplary placement of the left hand glove 38 and the right hand glove 40. The operation of the embodiment as depicted in FIGS. 3 and 4 is described in more detail herein with respect to the schematic diagram of FIG. 6. It is to be known that the fetal monitoring device 36 may show particular advantages in an application wherein the maternal patient is pregnant with twins and monitoring of the health of both fetuses is desired.

Figure 5A:
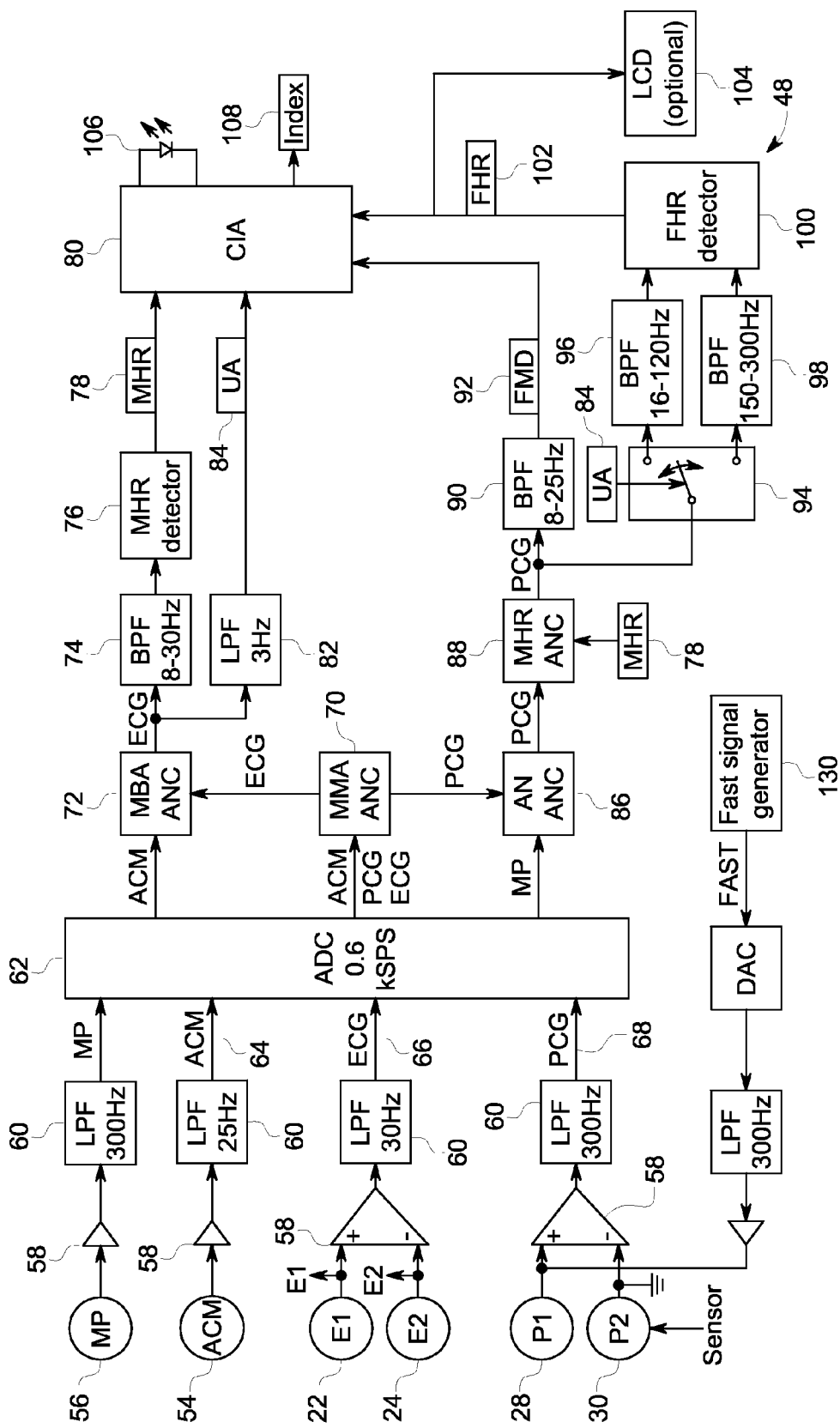
FIGS. 5A-C are schematic diagrams of an exemplary embodiment of a fetal monitoring device.
Figure 5B:
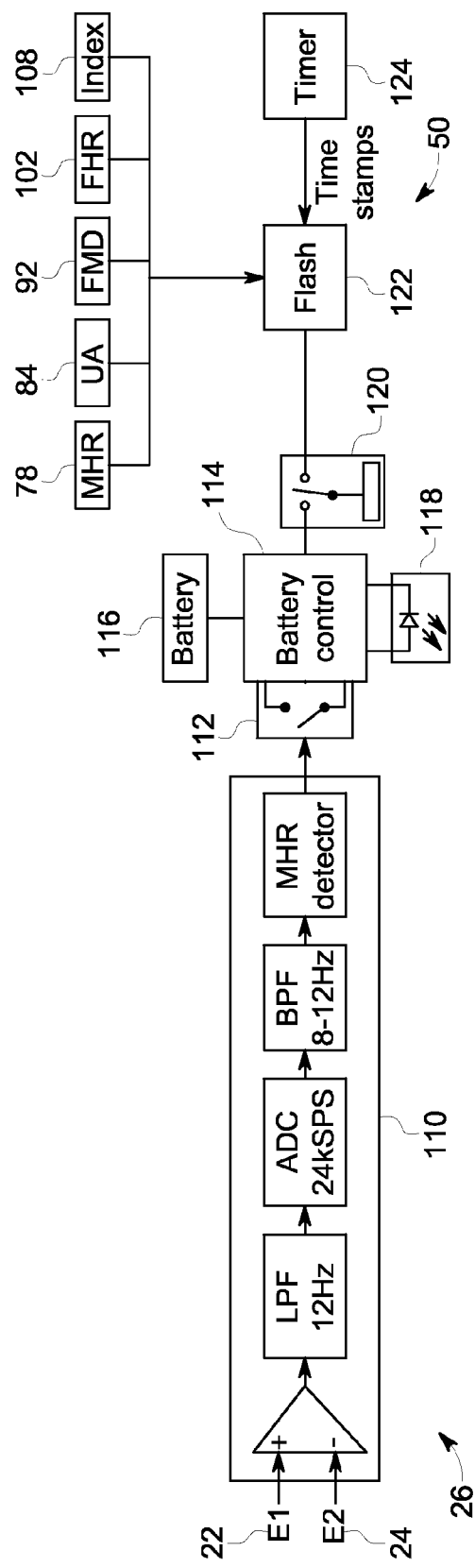
Figure 5C:
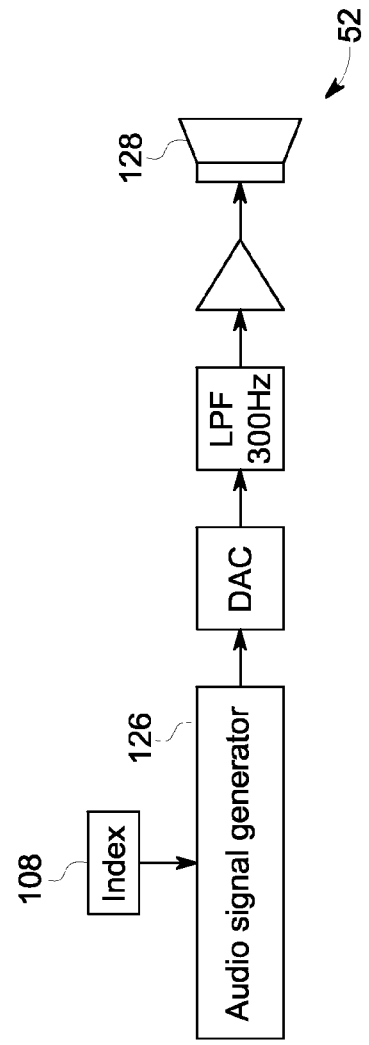

FIGS. 5A-C are schematic diagrams of an exemplary embodiment of a fetal monitoring device exemplarily such as described above with respect to FIGS. 1 and 2. It is to be understood that the circuitry depicted in FIGS. 5A-C exemplarily may be incorporated as part of the controller 26 as shown in FIGS. 1 and 2 and implemented in a combination of electronic hardware and software. The controller 26 as schematically shown in FIGS. 5A-C includes three portions, a signal processing portion 48 in FIG. 5A, a battery and data portion 50 in FIG. 5B, and an audio circuitry portion 52 in FIG. 5C.

Referring to the signal processing portion 48, the input as generally described above, including the first electrode 22, second electrode 24, first piezofilm contact 28 and second piezofilm contact 30 are shown. Additionally, optional additional inputs including an accelerometer 54 and a microphone 56 may be incorporated, as described herein. The inputs are provided to amplifiers 58 followed by low pass filters 60 before being provided to an analog digital converter (ADC) 62 to complete the signal pre-processing and digitization. It is to be noted that in an embodiment, the biopotentials acquired across first electrode 22 and second electrode 24 are provided to an amplifier 58 with a very high input impedance. In embodiments, the wires of the electrodes may be shielded. In embodiments as disclosed herein, the biopotentials acquired from first electrode 22 and second electrode 24 will be referred to as ECG 66; however, the ECG 66, as disclosed herein, may contain other biopotentials, including, but not limited to uEMG. In an embodiment, two input signals, namely ECG 66 and PCG 68, once digitized, are used in order to determine the index of fetal health. In a non-limiting embodiment, the sound obtained from the microphone 56 may be used for voice command input or adaptive noise cancellation (ANC). The acceleration signal (ACM) 64 (e.g. signal from accelerometer 54) may also be used for ANC.

ACM signal 64 is used to cancel maternal motion artifacts (MMA) from the PCG and ECG signals at MMA ANC 70. This adaptive noise cancelling blocks not only maternal, but also fetal movement artifacts. In an alternative embodiment, when the determination of fetal motion detection is enabled, the adaptive noise cancellation of 70 may be disabled and the maternal patient may be instructed to restrict her movement to limit maternal motion artifacts. At 72, adaptive noise cancellation is applied to remove maternal breathing artifacts (MBA ANC) from the ECG signal obtained after the MMA ANC. The MBA ANC 72 uses the accelerometer signal 64 which includes the maternal patient's respiration pattern on top of the maternal and fetal motion patterns.

The ECG signal, having been processed by MMA ANC 70 and MBA ANC 72, is provided to a band pass filter 74 exemplarily with a pass band of 8-30 Hz, which contains the main spectrum of the maternal ECG signal. The processed and filtered ECG signal is provided to a maternal heart rate detector 76, which determines the maternal heart rate (MHR) 78 from the processed and filtered ECG signal. It is to be noted that embodiments adaptive noise cancellation is not needed to remove the fetal heart rate from the processed ECG signal as the fetal ECG (f ECG) is comparatively very weak to the maternal component in the obtained ECG signal. The maternal heart rate 78 is provided to the computerized interpretation algorithms (CIA) 80, which, as described in further detail herein, determines an index of fetal health from the received parameters.

The ECG signals, having been processed by the MMA ANC 70 and the MBA ANC 72, are also provided to a low pass filter 82 exemplarily with a low pass cutoff of 3 Hz. This low frequency cutoff removes material and fetal electrocardiographic biopotentials leaving a uterine electromyographic (UEMG) signal. This filtered signal represents uterine activity 84 of the maternal patient which is also provided to the CIA 80.

The processed PCG signal from the MMA ANC 70 is provided to acoustic noise adaptive noise cancellation (AN ANC) 86. In an embodiment, one source of acoustic noise to the PCG signal may be the maternal patient's voice if the maternal patient is speaking during the monitoring. In some embodiments, the use of the external microphone 56 may provide the maternal voice to cancel from the processed PCG signal in the AN ANC 86. The processed PCG signal is provided to adaptive noise cancellation for maternal heart rate (MHR ANC) 88. The MHR ANC 88 may receive the calculated MHR 78 as described above. The noise being cancelled from the PCG signal through the MHR ANC 88 may be the noise contributed by the maternal abdominal blood vessels which are synchronized with the maternal pulse.

The processed PCG signal from the MHR ANC 88 is provided to a band pass filter 90 which exemplarily has a pass band between 8 and 25 Hz and the resulting signal represents the motion of the fetus for fetal motion detection (FMD) 92. The FMD 92 is provided to the CIA 80.

The processed PCG signal from the MHR ANC 88 is provided through a switch 94 that selects between first and second band pass filters. The switch receives the uterine activity 84 as described above and selects between the first band pass filter 96 and the second band pass filter 98 based upon whether or not the maternal patient is currently experiencing a contraction. If the maternal patient is not experiencing a contraction, then the switch 94 selects the first band pass filter 96 which exemplarily has a pass band between 16 and 120 Hz. If the maternal patient is experiencing a contraction, the switch 94 selects the second band pass filter 98 which exemplarily has a pass band between 150 and 300 Hz.

The PCG signal that has been filtered by the appropriately selected band pass filter is provided to a fetal heart rate (FHR) detector 100. The FHR detector 100 determines the FHR from the filtered PCG signal. It is to be noted that in exemplary embodiments, if the pass band between 150-300 Hz is selected, the amplitude of the fetal heart signal may be significantly lower versus the fetal heart signal found in the 16-120 Hz pass band. However, uterine activity spikes in the PCG signal can be effectively removed by removing frequencies below 150 Hz. The FHR detector 100 outputs the fetal heart rate 102. The FHR 102 is provided to the CIA 80. In an alternative embodiment, the FHR may be provided to an LCD display 104 incorporated as part of the fetal monitoring device in order to present the determined fetal heart rate.

It is to be noted that, in embodiments, adaptive noise cancellation is not necessary for umbilical noise when determining fetal heart rate as the umbilical noise is synchronized with the fetal heart rate. The fetal heart rate as determined in the manner described above has had artifacts due to maternal motion, maternal voice (or other acoustic noise), maternal abdominal vessel blood flow (synchronized with MHR) and uterine activity removed. In some embodiments, particularly if fetal motion detection (FMD) is disabled, fetal movement artifacts and material bowel noise may exist in the PCG signal. In an alternative embodiment, an autocorrelation of the PCG may additional be used to remove or reduce these remaining artifacts.

Thus, the CIA 80 is provided with the maternal heart rate 78, uterine activity 84, fetal motion detection 92, and fetal heart rate 102. The CIA 80 applies one or more algorithm, which may include neural network algorithm, fuzzy network algorithms, Dawes-Redman criteria, or other techniques in order to produce an index of fetal health. In one non-limiting embodiment, the algorithms applied by the CIA 80 seek to identify either reassuring patterns or non-reassuring patterns in the received maternal and fetal patient parameters. In one embodiment, the CIA 80 may solely discriminate between whether patterns are reassuring or non-reassuring and produce a binary output to that effect. In embodiments, it may be recognized that reassuring patterns may exist 97% or 99% of the time. In an alternative embodiment, the CIA 80 may break the non-reassuring patterns into a plurality of alert levels with various criteria identifying the alert level associated with the identified non-reassuring pattern. The table below provides a non-limiting example of various criteria that may be applied in order to identify non-reassuring patterns, in embodiments, and to evaluate the severity or required alert with respect to the identified non-reassuring pattern.

| Possible Alert Conditions | | |
|---|---|---|
| Level One Alert * | Level Two Alert ** | Level Three Alert *** |
| decreased variability | tachycardia (>180 bpm) | bradycardia (<90 bpm) |
| flat variability | bradycardia (90-99 bpm) | prolonged deceleration (<80 bpm) |
| bradycardia (100-119 bpm) | late decelerations | late, variable, or mixed decelerations with decreased variability and tachycardia or bradycardia |
| tachycardia (161-180 bpm) | severe variable or sporadic decelerations | |
| mild/moderate variable decelerations | tachycardia with flat variability | |
| mild/moderate sporadic decelerations | mild sporadic decelerations with decreased variability | severe late or variable decelerations with tachycardia or bradycardia or decreased variability |
| mild variable decelerations with creased variability or mild tachycardia or mild bradycardia | moderate variable decelerations with tachycardia or bradycardia or decreased variability | moderate bradycardia and flat variability |
| tachycardia (161-180 bpm) with decreased variability | mixed decelerations | any deceleration (except mild variables) and flat variability |
| undefined decelerations | mild bradycardia and flat variability | |
| mild bradycardia and decreased variability | mild late or mixed decelerations with decreased variability or mild tachycardia | late or severe variables with tetanic uterine contraction |
| prolonged deceleration (>120 bpm) | | |
| increased hypertonus | | |
| tetanic uterine contraction (>60 sec) | mild variables and flat variability | |
| signal quality | mild variables and mild tachycardia and decreased variability | |
| | prolonged deceleration (80-119 bpm) | |

The CIA 80 is connected to an LED 106 that may be operated in order to visually indicate the determined index of fetal health. In one embodiment, the LED 106 may be green if a reassuring pattern is identified and red if a non-reassuring pattern is identified. In an alternative embodiment, the LED 106 may be a multi-colored LED or a series of LEDs such that reassuring patterns are indicated with green, a level 1 alert indicated with yellow, a level 2 alert indicated with orange, and a level 3 alert indicated with red; however, a person of ordinary skill in the art will recognize other similar indication schemes based upon the determined index of fetal health. The CIA 80 may also output the determined fetal health index as a numerical value or other output 108. It is to be understood that in alternative embodiments, rather than a visual indication or in addition to a visual indication, an audible or tactile alert or indication may be provided to indicate that a non-reassuring pattern has been identified by the CIA 80.

Referring now to the battery and data portion 50 of the schematic diagram, in an embodiment, the controller 26 may be passively operated between sleep conditions or active conditions such as to conserve battery power. In one such embodiment, the system is operated to operate under a minimum power consumption until the maternal heart rate is detected at which point the battery power is used to operate the other functionalities. The maternal patient thus may activate the device by placing the sensors on her abdomen to obtain her ECG. In an embodiment independent heart rate circuitry 110 operates in parallel to the signal processing portion 48 and receives the ECG signals from the first electrode 22 and the second electrode 24. This independent MHR circuitry can be minimally powered from the battery without draining battery resources to the signal processing portion 48, when a maternal ECG is not present. In an embodiment, the CIA 80 resets each time a maternal ECG is found. A switch 112 receives the indication of maternal heart rate and operates with the battery control 114 to provide power to the signal processing portion 48 from the battery 116 at times when a maternal heart rate is detected. The battery control 114 can also be connected to a battery status LED 118 that indicates when the battery is low or requires recharge. In an embodiment, the circuitry is always on and requires a recharge or replacement to activate the circuitry. Additionally, a connector 120 such as a USB connector can be used to either provide power connection for powering controller 26 or recharging the battery 116 or to provide a data communication with the fetal monitoring device 10. The connector 120 may be connected to flash memory 122 that is configured to receive data collected and/or determined by the fetal monitoring device. Such data may include compressed signals ECG or PCG or compressed derived waveforms of MHR, UA, FMD, FHR or fetal health index. The connector 120 can also be used to enable or disable the fetal movement detection (FMD). In further embodiments, the flash memory 122 may store a log of events, such as power on, power off, and generation of fetal acoustic stimulation signals as will be described in further detail herein. The flash memory 122 may be connected to a timer 124 that provides time stamps for the events and determinations. In embodiments, the flash memory 122 can have a dedicated battery that provides power to the life of the device. The timer 124 may be set to Greenwich Time and maintain time for the life of the device.

Referring now to the audio circuitry portion 52, in alternative embodiments, an audio signal generator 126 may be connected through circuitry to a speaker 128 such as to present audible indications of the determined index of fetal health. In an alternative embodiment, the controller 26 may operate such as to provide basic instructions to the maternal patient for operation and use of the fetal monitoring device, including an audible signal to place and/or remove the sensors (which may be incorporated into a glove or gloves as described above) from the abdomen of the maternal patient according to a particular time for signal acquisition. This timing may be defined by one or more algorithms used by the CIA 80 to determine the index of fetal health.

In embodiments after the audio signal to place the sensors on the abdomen of the patient is provided, the system may operate to produce a vibro-acoustic stimulation signal. A fetal acoustic stimulation (FAST) signal generator 130 operates the piezofilm to generate an acoustic signal projected into the maternal patient's abdomen such as to stimulate or wake up the fetus for effective fetal monitoring. This is achieved by applying a signal from the FAST generator 130 to first piezofilm contact 28 and second piezofilm contact 30 to operate the piezofilm as a speaker. In a still further embodiment, the FAST signal generator 130 is operated to generate an acoustic stimulation signal to reduce testing time of non-stress tests, exemplarily during antepartum surveillance.

Figure 6:
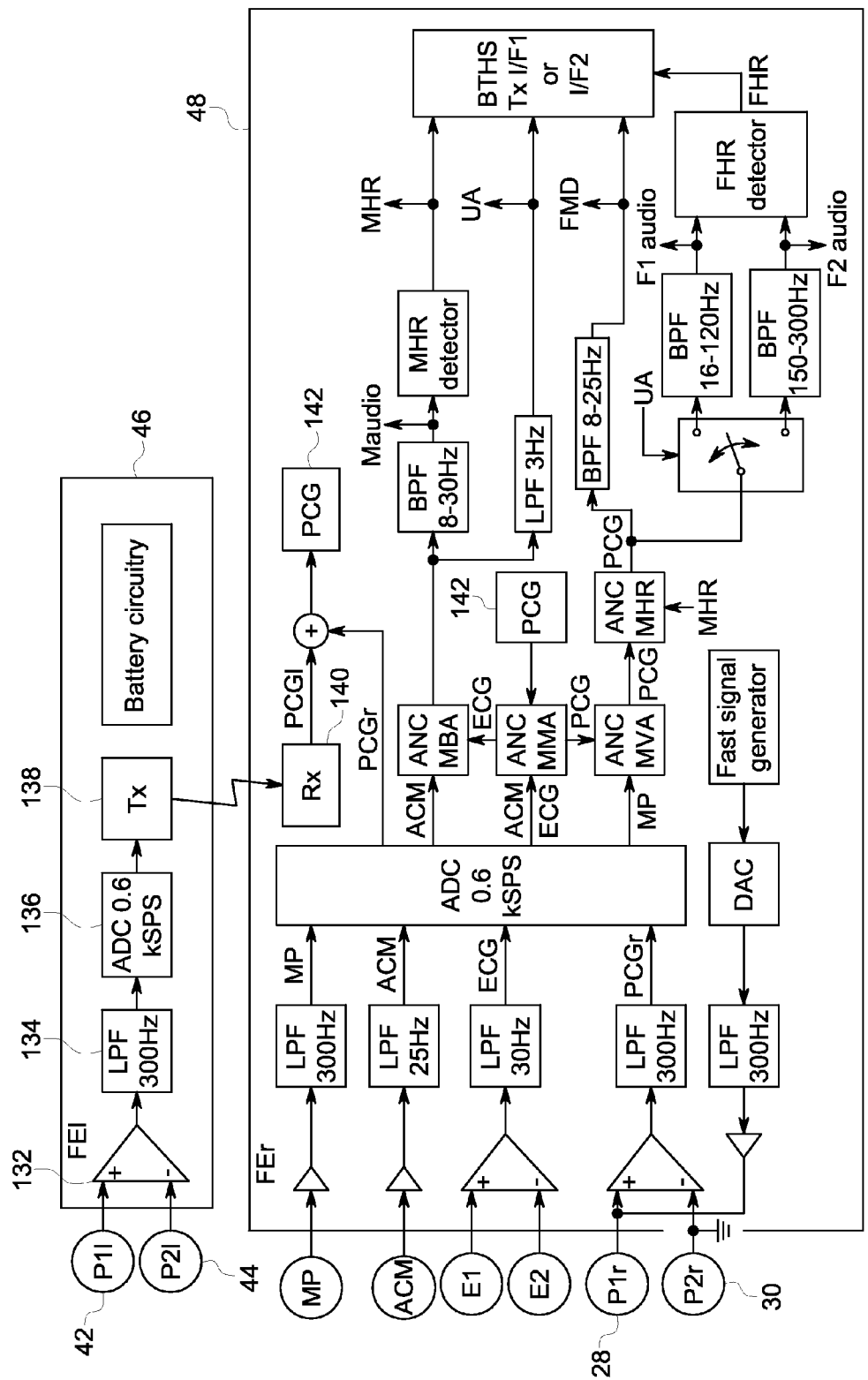
FIG. 6 is a schematic diagram of an alternative exemplary embodiment of a fetal monitoring device.

FIG. 6 is a schematic diagram of an alternative exemplary embodiment of a fetal monitoring device such as depicted in FIGS. 3 and 4 as described above. It is to be noted that much of the signal processing portion 48 depicted in FIG. 6 is similar to that as described above with respect to FIG. 5A and therefore the description of FIG. 5 above is referred for those portions. It is further noted that while not depicted, embodiments of the battery and data portion 50 as shown in FIG. 5B and audio circuitry portion 52 as shown in FIG. 5C may also be used in connection with the signal processing portion 48 of FIG. 6. It is to be noted that in the embodiment depicted in FIG. 6, a second piezofilm with third piezofilm contact 42 and fourth piezofilm contact 44 acquire a second PCG signal, exemplarily noted as PCGL. The PCG obtained from the first piezofilm contact 28 and the second piezofilm contact 30 is herein referred to as PCGR.

The PCGL signals acquired by the third piezofilm contact 42 and the fourth piezofilm contact 44 are provided to an amplifier 132, a low pass filter 134 and an analog to digital converter 136 (running e.g. at 600 samples per second) for basic signal processing, and to a wireless transmitter 138. The wireless transmitter 138 transmits the obtained pre-PCGL signal to a wireless receiver 140 incorporated in the signal processing portion 48. In an exemplary embodiment, the wireless transmission between transmitter 138 and receiver 140 may be performed using wireless body area network (WBAN). After the receiver 140 receives the PCGL signal, the PCGL and PCGR signals are combined to provide the PCG signal 142 as used in the signal processing portion 48 and as described above. In an embodiment for monitoring of twin fetuses, the PCGL and PCGR signals may alternatively be processed separately in the manner described above with respect to FIG. 5.

Figure 7:
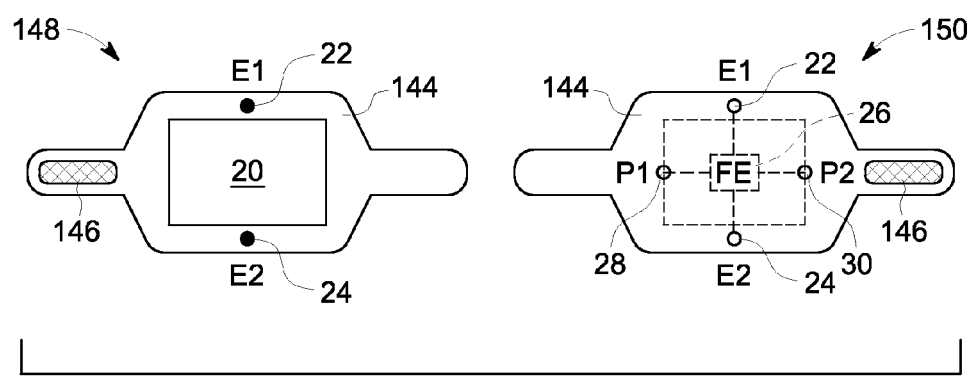
FIG. 7 depicts front and back views of an alternative exemplary embodiment of a fetal monitoring device.

FIG. 7 depicts front and back views of an alternative exemplary embodiment of a fetal monitoring device wherein the fetal monitoring device is incorporated into a belt 144 to be worn by the patient. The belt 144 may include hook and loop fasteners 146 that secure the belt 144 to the patient. On the front side 148 of the belt 144 the dry first electrode 22 and dry second electrode 24 and the piezofilm 20 are exposed for contact with the maternal patient's abdomen. On the reverse side 150 of the belt 144, the controller 26 and the first piezofilm contact 28, second piezofilm contract 30 are depicted.

Figure 8:
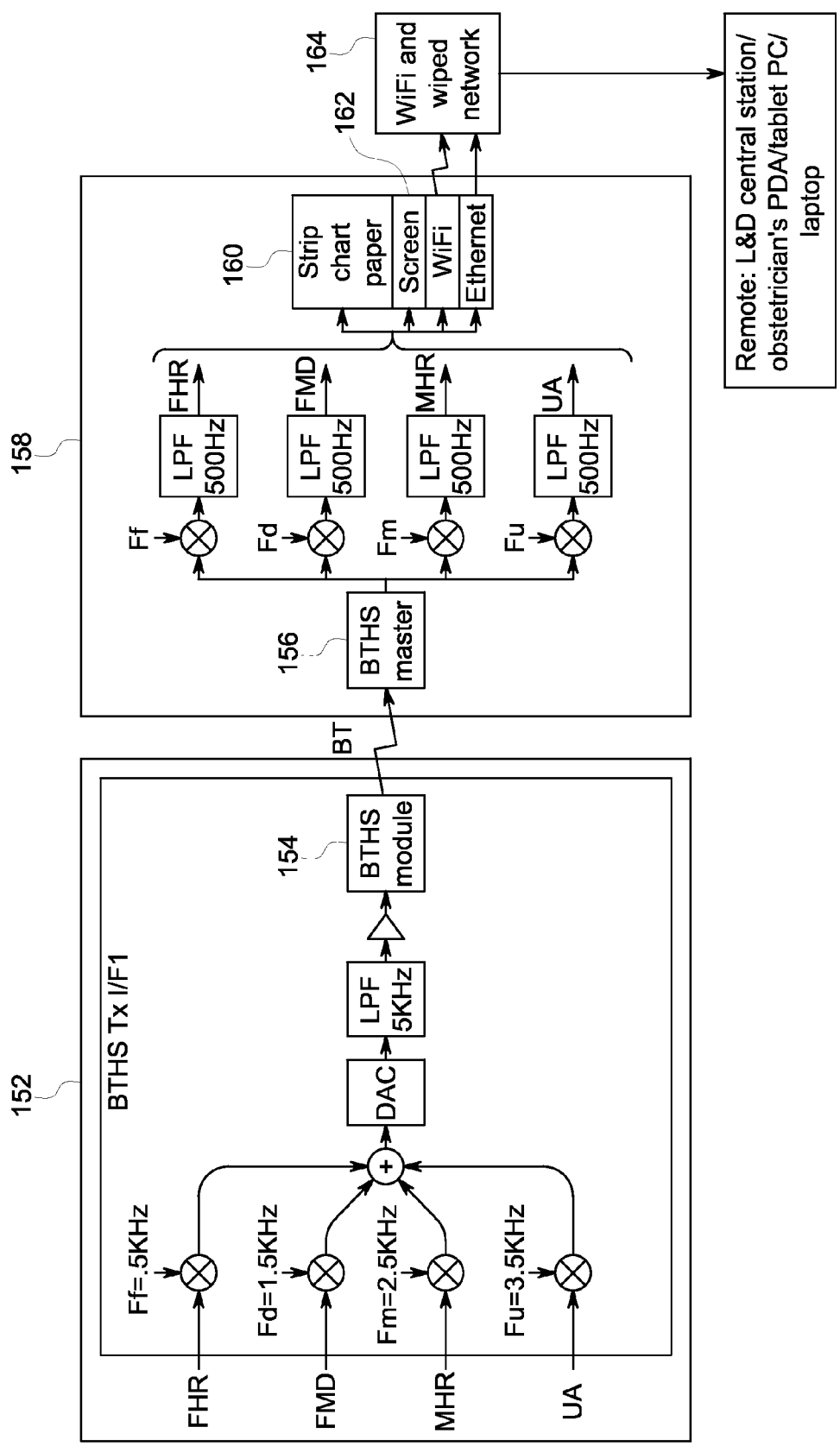
FIG. 8 is a schematic diagram of an exemplary embodiment of a fetal monitoring system.

FIG. 8 is a schematic diagram of a still further exemplary embodiment of a fetal monitoring system, wherein the fetal monitoring device is operated as a transducer in addition to its use as a standalone device described above. Therefore, embodiments of the fetal monitoring device 152 can obtain FHR, FMD, MHR, and UA as described above with the additional features described herein to add further transmission capability. Such functionality may facilitate use of the fetal monitoring device in the clinical setting, both as a maternal patient operated screening tool, but also to collect the FHR, FMD, UA, and MHR tracings required by trained nurses or doctors to expertly interpret the condition of the mother and fetus in terms of a non-reassuring or reassuring pattern. Namely, the fetal monitoring device 152 is used to determine the FHR, FMD, MHR, UA parameters in addition to the index of fetal health and the determined parameters of FHR, FMD, MHR, and UA are transmitted to a bedside or locally operated computer or system such that the signals and parameters determined by the fetal monitoring device may be used in the clinical setting for their own value apart from the determination of the index of fetal health.

In general, a Bluetooth headset transmission module (BTHS) 154, as used and described herein, has a microphone input and at least 4 KHz bandwidth to transfer audio signals. The BTHS software stack includes multiple Bluetooth audio profiles that provide reliance real-time transmission of audio signals at distances suitable for use in a maternal labor and delivery room (approximately 10 meters) or a maternal labor and delivery ward (approximately 100 meters). Many computers currently available at obstetrician offices, labor and delivery rooms, labor and delivery wards, laptop, tablets, or PDAs have built in Bluetooth headset master modules that support audio communication with a Bluetooth headset module. The frequency bandwidth of the four waveforms focused on in the present disclosure (FHR, HMD, MHR, and UA) is much less than the available 4 KHz bandwidth available through the BTHS module. Therefore, frequency division multiplexing (FDM) is possible for multiple fetal waveforms through one BTHS channel. The four waveforms (FHR, FMD, UA, and MHR) can be modulated at different carrier frequencies (e.g. FF, FD, FM, and FU) and mixed together to be provided to the microphone input of the BTHS module 154. Upon receipt by the receiving computer, the mixed audio signal from the BTHS master module can be demodulated using the same carrier frequencies and low pass filters so that the waveforms can be recovered to be presented in various manners as discussed in further detail herein.

In one embodiment, the FHR, FMD, MHR, and UA are converted to audio signals and transmitted using the BTHS module 154 that wirelessly transmits a signal to a Bluetooth headset receiving master module 156 implanted in the locally operated computer 158. Such locally operated computer may be an in room desktop, laptop, tablet computer or a wireless receiver router. The locally operated computer can then present the determined physiological parameters in a strip chart presentation either on paper 160 or on a screen 162. The locally operated computer 158 may then be connected to a hospital information network 164 either through a Wi-Fi or Ethernet connection and the determined physiological parameters can be sent to or stored at another remote location, including, but not limited to a labor and delivery central station, and obstetrician PDA, tablet PC or laptop.

Figure 9:
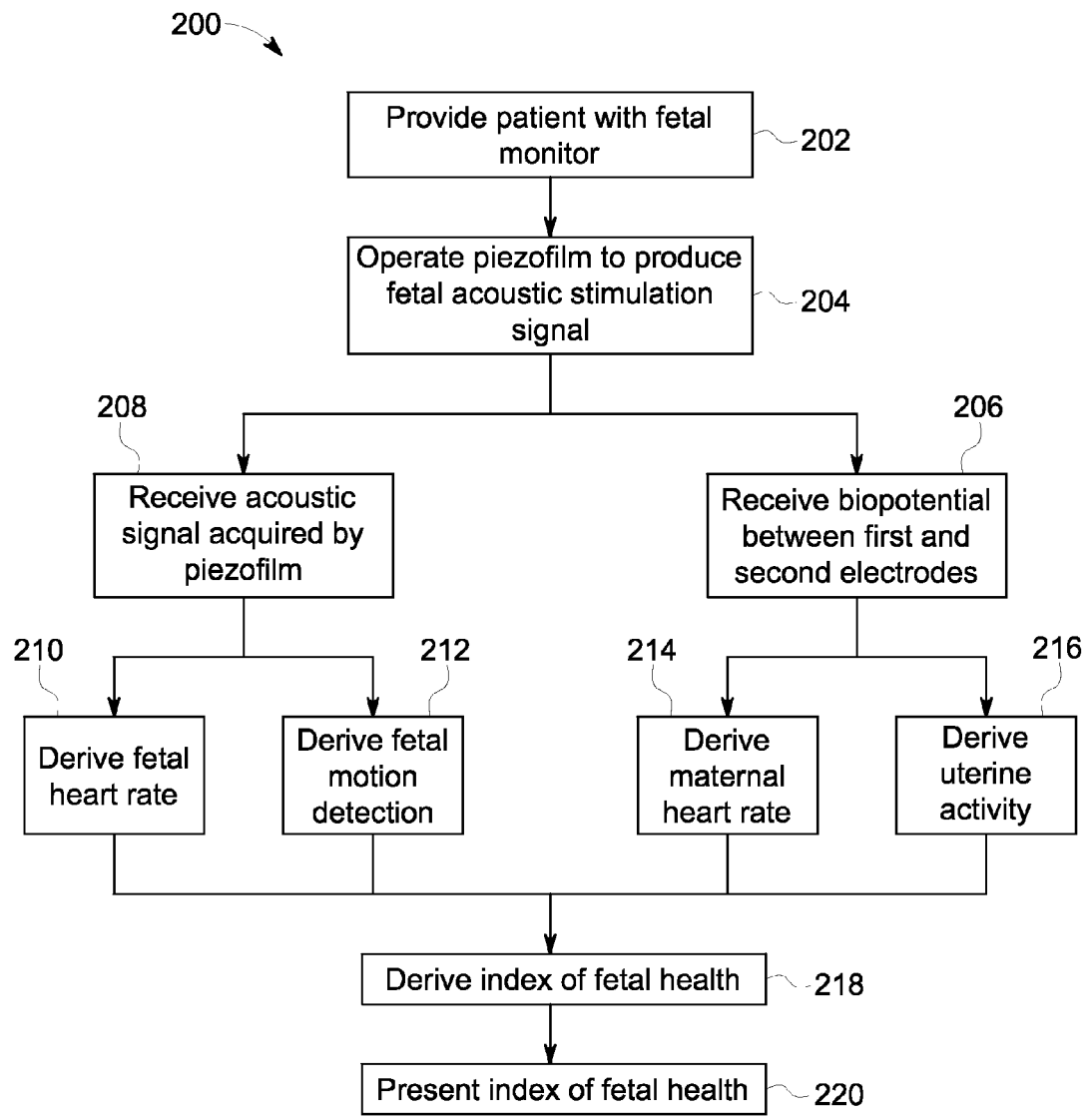
FIG. 9 is a flow chart that exemplarily depicts an embodiment of a method of monitoring the health of a fetus.

FIG. 9 is a flow chart that exemplarily depicts an embodiment of a method of monitoring the health of a fetus 200. At 202 the maternal patient is provided with a fetal monitor that exemplarily is configured in accordance with that as described above. In one such embodiment, the maternal patient wears the fetal monitoring device and in still further embodiments, the fetal monitoring device may provide a signal to initiate a fetal monitoring or may operate in a sleep or low power mode until the presence of a maternal heart rate is determined at which point the fetal monitor may operate in full power mode.

The fetal monitor may operate the piezofilm to produce a fetal acoustic stimulation signal at 204. The piezofilm is operable both as a speaker and as a microphone and therefore, by reversing the voltage across the piezofilm, the piezofilm can be operated to produce an acoustic wave or waves that "wakes up" or stimulates the fetus as such may produce improved monitoring of fetal health during non-stress tests antepartum. After the fetus has been stimulated, the fetal monitoring device receives a biopotential between the first and second electrodes at 206 and receives an acoustic signal acquired by the piezofilm at 208. It is to be noted that in embodiments, the first and second electrodes are dry electrodes and therefore do not require any conductive gel or other conductor in order to obtain the desired biopotentials.

One or more of a fetal heart rate at 210 and a fetal motion detection at 212 are derived from the received acoustic signal from piezofilm at 208. Embodiments of the derivation of the fetal heart rate at 210 and the fetal motion detection at 212 are described above. Similarly, one or more of a maternal heart rate at 214 and a uterine activity at 216 are derived from the biopotential between the first and second electrodes at 206. Exemplary embodiments of the derivation of the maternal heart rate at 214 and the uterine activity at 216 are also described above.

An index of the fetal health is derived at 218 from at least one of the fetal heart derived at 210 and fetal motion detection derived at 212 and at least one of the maternal heart rates derived at 214 and the uterine derived at 216. It is to be noted that in alternative embodiments, all four of the fetal heart derived at 210, fetal motion detection derived at 212, maternal heart rate derived at 214, and the uterine activity derived at 216 are used in deriving the index of fetal health at 218. In a still further embodiment, the fetal motion detection at 212 is not derived and yet the other three parameters of fetal heart rate, maternal heart rate, or uterine activity are used to derive the index of fetal health at 218. In another embodiment, FHR 210, FMD 212, and MHR 214 are used to conduct a non-stress test antepartum. In some implementations of this embodiment, a FAST signal may be generated (not depicted) as described above. In an additional embodiment, only FHR and MHR are used in a non-stress test antepartum to derive the index of fetal health. In still further embodiments, other sensed signals such as an acceleration signal, or an ambient noise signal from a microphone, can be used to derive parameters or the index of fetal heath in manners as described above.

At 220 the index of fetal health is presented to the maternal patient. The index of fetal health can be presented in a variety of ways both visually, acoustically, or tactilely. In some embodiments, the index fetal health can be reported with the lighting of LEDs, while in other embodiments, the index of fetal health could be presented on an LCD display.

Embodiments as disclosed herein provide a patient operated transducer and signal processing device that is easy for a maternal patient to operate and understand. The disclosed device uses two passive technologies in PCG and ECG in a way in which both technologies are integrated to maximize the strengths of these technologies in a manner not found in the field of fetal monitoring. In particular, abdominal ECG is used to detect maternal ECG and uterine EMG signals from which maternal heart rate and uterine activity are derived and the abdominal ECG is not used to detect the comparatively much weaker fetal ECG signal. Similarly, PCG is used to detect the strong fetal acoustic signal and to detect fetal motion. A breathing artifact and maternal/fetal motion (movement) artifacts are cancelled to improve the quality of the uterine activity detection from the uterine EMG signals found underlying the abdominal ECG signal. Breathing and motion artifacts are cancelled to improve the quality of the maternal heart rate detected over maternal ECG signals found underlying the abdominal ECG signal. Motion artifact, maternal voice artifact, maternal abdominal pulse artifact, and uterine activity noise are cancelled in order to improve the quality of the fetal heart rate detected over PCG. Maternal voice artifacts and maternal abdominal pulse artifacts are cancelled to improve the quality of fetal motion detection defected over PCG. Therefore, the parameters derived from the abdominal ECG signal are used to improve the quality of the parameters derived from the PCG signal.

Embodiments of the fetal monitoring device disclosed herein use both a piezofilm and dry electrodes, neither of which require gel or any form of skin preparation in order to acquire the ECG or PCG signals as used in the fetal monitoring device. As the piezofilm covers a substantial portion of the abdomen, the fetal acoustic signal sensed by the piezofilm is largely independent of the fetal presentation within the uterus and the relatively large area of piezofilm increases the signal to noise ratio in the PCG signal as the acoustic signal from the fetal heart propagates in all directions. Therefore, the large antenna provided by the area of the piezofilm results in a stronger output signal acquired by the piezofilm. The phase delay of acoustic signals from the fetal heart at any two sensing points on the piezofilm is insignificant due to the fact that the sound speed in the abdomen is much higher than f×d where f equals 300 Hz as the cutoff frequency of the PCG low pass filter and d is less or equal to 0.1 meter which is the maximum difference between two distances from the fetal heart to any two sensing points of the piezofilm. Therefore, the fetal heart signal as sensed by the piezofilm with a larger sensing area is not corrupted by the spatial position of the fetal heart relative to the transducer. A fetal heart signal with a high signal to noise ratio is beneficial particularly in monitoring an obese maternal patient, monitoring a fetus as the fetus moves within the uterus, and to detect fetal heart rate accurately in the back ground of other noise, including bowel noise artifacts. The embodiments of the fetal monitoring device utilize dry electrodes as no gel or skin preparation is required and the abdominal signals of maternal ECG and uterine EMG has a range of action potentials from tens to hundreds of microvolt and therefore, the signals to be acquired can be picked up with dry electrodes without gel or skin preparation. With the elimination of the need for gel or skin preparation, no adhesive patches need be used to keep sensors on the abdomen and the new monitoring device can be applied and removed by the maternal patient as needed or as desired or comfortable to the maternal patient.

Embodiments as presently disclosed herein provide additional benefits as currently used Doppler techniques are susceptible to motion artifacts whereas the technologies as described herein are more resilient to such artifacts. As described above, the FHR as determined by PCG is independent of fetal position in the uterus which reduces or minimizes signal loss in FHR determination. In embodiments as disclosed herein, the fetal monitoring device (due to CIA) requires little, if any, skills, education, or training such as is currently required with Doppler ultrasound and tocodynamometry to analyze and interpret the fetal heart rate and uterine activity as provided by those tracings.

As described above, PCG provides a relatively strong fetal heart signal even for obese patients due to a large sensing area of the piezofilm in the disclosed fetal monitoring device. Furthermore, abdominal ECG can be used in environments to provide good detection of maternal heart rate and uterine activity even in obese patients.

As described above, the piezofilm and the electrodes in embodiments of the fetal monitoring device as disclosed herein do not require any conductive gel or skin preparation as the piezofilm does not need gel at all and the dry electrodes as disclosed provide low skin-electrode impedance sufficient to sense the comparatively strong maternal ECG and uterine EMG signals without gel. Additionally, the use of the disclosed ECG and PCG eliminates the need for conventional cardiotocography which relies on the semi-invasive Doppler ultrasound technology in contrast to the passive PCG technology. Embodiments of the fetal monitoring device as disclosed herein use passive technologies and incorporate a sleep or low power mode when a maternal pulse is not detected and only operate the fetal monitoring device at times when a maternal pulse is present. These features minimize battery use and maximize battery life.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fetal monitoring device, comprising:
   a piezofilm sheet;
   a first electrode;
   a second electrode;
   a controller operably connected to the piezofilm sheet, the first electrode and the second electrode, the controller receives an acoustic signal from the piezofilm sheet and a biopotential measured between the first electrode and the second electrode and derives at least one of fetal heart rate and fetal motion detection from the acoustic signal and at least one of maternal heart rate and uterine activity from the biopotential and derives an index of fetal health from the at least one of fetal heart rate and fetal motion detection and at least one of maternal heart rate and uterine activity; and
   an indicator operable by the controller to present the derived index of fetal health.

2. The fetal monitoring device of claim 1, wherein the fetal monitoring device is incorporated into at least one glove to be worn by a patient.

3. The fetal monitoring device of claim 1, wherein the first electrode and the second electrode are dry electrodes.

4. The fetal monitoring device of claim 1, wherein the controller operates the piezofilm sheet as a speaker to generate a fetal acoustic stimulation signal.

5. The fetal monitoring device of claim 1, wherein the controller derives both the fetal heart rate and the fetal motion detection from the acoustic signal and derives both the maternal heart rate and the uterine activity from the biopotential and calculates the index of fetal health from the fetal heart rate, fetal motion detection, maternal heart rate, and the uterine activity.

6. The fetal monitoring device of claim 5, wherein the calculated index of fetal health is an alert severity, the indicator is at least one LED, and the indicator presents an indication of the alert severity.

7. The fetal monitoring device of claim 5, further comprising an accelerometer that produces an acceleration signal, wherein the controller receives the acceleration signal and removes breathing and motion artifacts from the biopotential and motion artifacts from the acoustic signal based upon the acceleration signal.

8. The fetal monitoring device of claim 5, further comprising a microphone that acquires an ambient sound signal, wherein the controller receives the ambient sound signal and removes external sound artifacts from the acoustic signal based upon the ambient sound signal.

9. The fetal monitoring device of claim 5, wherein the controller removes abdominal pulse artifacts from the piezofilm signal based upon the derived maternal heart rate, and selects a pass band for the piezofilm signal based upon the derived uterine activity before the fetal heart rate is derived from the piezofilm signal.

10. The fetal monitoring device of claim 1, further comprising a wireless transmitter connected to the controller, and the wireless transmitter broadcasts the fetal heart rate, fetal motion detection, maternal heart rate, the uterine activity, and the index of fetal health.

11. A fetal monitoring device, comprising:
at least one glove configured to be worn by a patient, the glove having a forehand side, a backhand side, a thumb region, and at least one finger region;
a piezofilm sheet secured to an exterior of the forehand side of the at least one glove;
a first electrode secured to the forehand side of the thumb region;
a second electrode secured to the forehand side of at least one finger region;
a controller electrically connected to the piezofilm, first electrode, and the second electrode, the controller receives a piezofilm signal from the piezofilm sheet and a biopotential measured between the first electrode and the second electrode and derives a fetal heart rate and a fetal motion detection from the piezofilm signal and derives a maternal heart rate and a uterine activity from the biopotential and derives an index of fetal health from the fetal heart rate, the fetal motion detection, the maternal heart rate, and the uterine activity; and
an indicator operable by the controller to present the index of fetal health.

12. The fetal monitoring device of claim 11, wherein the indicator is an LED device operable to produce at least three visual indications of different levels of the index of fetal health.

13. The fetal monitoring device of claim 12, wherein the controller and the indicator are incorporated into the backhand side of the at least one glove.

14. The fetal monitoring device of claim 13, further comprising a wireless transmitter connected to the controller, and the wireless transmitter broadcasts the fetal heart rate, fetal motion detection, maternal heart rate, the uterine activity, and the index of fetal health.

15. The fetal monitoring device of claim 11, wherein the controller is operable to operate the piezofilm in a first mode wherein the piezofilm collects acoustical data as the piezofilm signal and operate the piezofilm in a second mode wherein the piezofilm produces a fetal acoustic stimulation signal.

16. A method of monitoring the health of a fetus, the method comprising:
providing a mother with a wearable garment that comprises a piezofilm sheet, a first electrode, a second electrode, and a controller;
receiving at the controller a biopotential between the first electrode and the second electrode;
receiving at the controller an acoustic signal from the piezofilm;
deriving with the controller at least one of fetal heart rate and fetal motion detection from the received acoustic signal,
deriving with the controller at least one of maternal heart rate and uterine activity from the received biopotential;
deriving an index of fetal health from the derived at least one of fetal heart rate and fetal motion detection and at least one of maternal heart rate and uterine activity;
visually presenting the index of fetal health.

17. The method of claim 16, further comprising:
operating the piezofilm with the controller to produce a fetal acoustic stimulation signal;
then operating the piezofilm with the controller to acquire the acoustic signal from the piezofilm.

18. The method of claim 16, wherein the wearable garment is at least one glove.

19. The method of claim 16, wherein the index of fetal health is visually presented by illuminating an LED of the wearable garment.

20. The method of claim 16, further comprising:
frequency division multiplexing the fetal heart rate, fetal motion detection, maternal heart rate, and uterine activity;
frequency modulating each of the fetal heart rate, fetal motion detection, maternal heart rate, and uterine activity at a different carrier frequency;
wireless transmitting the modulated and multiplexed fetal heart rate, fetal motion detection, maternal heart rate, and uterine activity with a wireless transmitter of the wearable garment to a monitoring device;
receiving the fetal heart rate, fetal motion detection, maternal heart rate, and uterine activity at the monitoring device;
demodulating the modulated fetal heart rate, fetal motion detection, maternal heart rate, and uterine activity;
visually presenting the fetal heart rate, fetal motion detection, maternal heart rate, and uterine activity at the monitoring device.

* * * * *